(12) United States Patent
Borgmann et al.

(10) Patent No.: US 7,645,914 B2
(45) Date of Patent: Jan. 12, 2010

(54) METHOD FOR THE TELOMERIZATION OF NON-CYCLIC OLEFINS

(75) Inventors: Cornelia Borgmann, Frankfurt (DE); Dirk Roettger, Recklinghausen (DE); Dagmara Ortmann, Brig-Glis (DE); Reiner Bukohl, Marl (DE); Stephan Houbrechts, Duffel (BE); Franz Nierlich, Marl (DE)

(73) Assignee: Evonik Oxeno GmbH, Marl (DE)

( * ) Notice: Subject to any disclaimer, the term of this patent is extended or adjusted under 35 U.S.C. 154(b) by 220 days.

(21) Appl. No.: 11/574,060

(22) PCT Filed: Aug. 23, 2005

(86) PCT No.: PCT/EP2005/054136
§ 371 (c)(1),
(2), (4) Date: Feb. 22, 2007

(87) PCT Pub. No.: WO2006/024615
PCT Pub. Date: Mar. 9, 2006

(65) Prior Publication Data
US 2007/0213574 A1    Sep. 13, 2007

(30) Foreign Application Priority Data
Aug. 28, 2004  (DE) .................. 10 2004 041 778
Aug. 1, 2005    (DE) .................. 10 2005 036 038

(51) Int. Cl.
*C07C 2/02* (2006.01)
*C07C 2/38* (2006.01)

(52) U.S. Cl. .............. 585/507; 585/506; 585/520; 585/527; 585/531; 585/601

(58) Field of Classification Search ............. 585/277, 585/506, 507, 520, 527, 531
See application file for complete search history.

(56) References Cited

U.S. PATENT DOCUMENTS

| | | |
|---|---|---|
| 5,177,282 A | 1/1993 | Nierlich et al. |
| 7,002,053 B2 | 2/2006 | Nierlich et al. |
| 7,026,523 B2 | 4/2006 | Rottger et al. |
| 7,030,286 B2 | 4/2006 | Rottger et al. |
| 7,115,790 B2 | 10/2006 | Beller et al. |
| 7,161,053 B2 | 1/2007 | Beckmann et al. |
| 2004/0242947 A1 | 12/2004 | Beller et al. |

(Continued)

FOREIGN PATENT DOCUMENTS

DE    101 49 348 A1    4/2003

(Continued)

OTHER PUBLICATIONS

U.S. Appl. No. 12/088,041, filed Mar. 25, 2008, Weise, et al.

(Continued)

*Primary Examiner*—In Suk Bullock
(74) *Attorney, Agent, or Firm*—Oblon, Spivak, McClelland, Maier & Neustadt, L.L.P.

(57) ABSTRACT

Process for telomerizing noncyclic olefins having at least two conjugated double bonds with at least one nucleophile using a catalyst containing a metal of group 8, 9 or 10 of the Periodic Table of the Elements, wherein hydrogen is added via a hydrogen source to the process in at least one process step in the overall telomerization process.

17 Claims, 1 Drawing Sheet

U.S. PATENT DOCUMENTS

2005/0240039 A1 10/2005 Rottger et al.
2006/0058514 A1 3/2006 Röttger et al.
2006/0281959 A1 12/2006 Krissmann et al.

FOREIGN PATENT DOCUMENTS

WO WO 91/09822 7/1991
WO WO 03/031378 * 4/2003

OTHER PUBLICATIONS

U.S. Appl. No. 11/574,063, filed Feb. 22, 2007, Nierlich, et al.
U.S. Appl. No. 11/574,018, filed Feb. 21, 2007, Borgmann, et al.
U.S. Appl. No. 10/588,762, filed Jan. 1, 2007, Wiese, et al.
U.S. Appl. No. 11/721,978, filed Jun. 16, 2004, Beller, et al.
U.S. Appl. No. 12/159,957, filed Jul. 2, 2008, Baumgarten, et al.
U.S. Appl. No. 10/593,330, filed Sep. 19, 2006, Borgmann, et al.
U.S. Appl. No. 12/307,331, filed Jan. 2, 2009, Brehme, et al.

* cited by examiner

Fig. 1

METHOD FOR THE TELOMERIZATION OF NON-CYCLIC OLEFINS

The invention relates to a process for telomerizing noncyclic olefins having at least two conjugated double bonds, in particular to the preparation of 1-octa-2,7-dienyl derivatives, by reacting a 1,3-butadiene-containg hydrocarbon mixture, in particular crack $C_4$, with nucleophiles.

The telomenization products which are formed from two moles of 1,3-butadiene and one mole of nucleophile (unsaturated amines, unsaturated alcohols and their esters and ethers) are starting materials for organic syntheses. The oxygen-containing derivatives are precursors for the preparation of linear $C_8$-alcohols and $C_8$-olefins, in particular 1-octanol and 1-octene. 1-Octanol in turn is used, for example, to obtain plasticizers. 1-Octene is a valuable comonomer for the modification of polyethylene and polypropylene.

The telomerization of butadiene with a nucleophile to give octadienyl derivatives is catalyzed by metal complexes, in particular palladium, compounds.

Examples of telomerization reactions are described, inter alia, in E. J. Smutny, J. Am. Chem. Soc. 1967, 89, 6793; S. Takahashi, T. Shibano, N. Hagihara, Tetrahedron Lett. 1967, 2451; EP-A-0 561 779, U.S. Pat. No. 3,499,042, U.S. Pat. No. 3,530,187, GB 1 178 812, NL 6 816 008, GB 1 248 593, U.S. Pat. No. 3,670,029, U.S. Pat. No. 3,670,032, U.S. Pat. No. 3,769,352, U.S. Pat. No. 3,887,627, GB 1 354 507, DE 20 40 708, U.S. Pat. No. 4,142,060, U.S. Pat. No. 4,146,738, U.S. Pat. No. 4,196,135, GB 1 535 718, U.S. Pat. No. 4,104,471, DE 21 61 750 and EP-A-0 218 100.

The feedstocks used for the preparation of octadienyl derivatives may be pure 1,3-butadiene or 1,3-butadiene-containing hydrocarbon mixtures, for example crack $C_4$.

Owing to the costly and inconvenient removal process, 1,3-butadtene is a relatively expensive feedstock. It is therefore usually more economically viable to select 1,3-butadiene-containing hydrocarbon mixtures as the feedstock for the telomenrization This is possible since most of the accompanying substances such as saturated hydrocarbons, for example n-butane or isobutane, or monoolefins for example isobutene and linear butenes, behave inertly in the telomerization reaction. Only inhibitors, i.e. substances which reduce the space-time yield or the selectivity or increase the catalytic consumption, should be removed beforehand, According to DE 195 23 335, it is advisable, when using the $C_4$ fraction from naphtha crackers as the 1,3-butadiene-containing raw material, to limit the concentration of acetylenic compounds and of allenes in the reactant for the telomerization. The sum of acetylenically and allenically unsaturated compounds should not exceed 1% by mass based on 1,3-butadiene. For the removal of these troublesome components, reference is made to known processes without mentioning or citing particular processes.

With reference to this patent (DE 195 23 335), DE 101 49 348, DE 102 29 290 and DE 103 29 042 indicate, without specifying concentration limits, that it is favorable to remove acetylenic and allenic compounds before the telomerization.

WO 91/09822 states that it is appropriate to remove acetylenicaily unsaturated compounds, when they are present, by selective hydrogenation from the $C_4$ mixture obtained in the cracking process of naphtha, gas oil or LPG. The hydrogenation process used is not disclosed. In the examples, a raw material having a total content of acetylenes below 60 ppm is used and does not contain anly specified content of allenes.

The acetylenic compounds can be removed by extraction or hydrogenation of these compounds. In the removal of the acetylenic compounds (methylacetylene(propyne), ethylacetylene(butyne), vinylacetylene(butenyne)) by hydrogenation, processes are employed in which the acetulenic compounds are hydrogenated with high selectivity substantially without hydrogenation of 1,3-butadiene and monoolefins. The catalysts used are hydrogenation catalysts which comprise copper, copper in combination with base metals, copper in combination with noble metals or metal catalysts of metals of transition group VIII of the Periodic Table of the Elements, for example palladium catalysts. Corresponding processes are described, inter alia, in the following patets: U.S. Pat. Nos. 6,576,588, 6,417,419, 6,225,515, 6,015,933, 6,194,626, 6,040,489, 4,493,906, 4,440,956, 4,101,451, 3,912,789, 3,751,508, 3,541,178, 3,327,013, 3,218,268, EP 1 217 060, EP 1 151 790, EP1 070 695, EP 0 273 900, NL 6 613 942.

The removal of allenes, especially of 1,2-butadiene, by hydrogenation is substantially more difficult than the selective removal of acetylenic compounds. The reactivity of 1,2-butadiene in the hydrogenation is only slightly higher than that of 1,3-butadiene, Therefore. 1,3 butadiene losses are unavoidable in the removal of 1,2-butadiene from 1,3-butadiene-containing hydrocarbon mixtures by hydrogenation.

For example, WO 98/12160 details a process for simultaneously removing acetylenic compounds and 1,2-butadiene frEom a 1,3-butadiene-containing hydrocarbon stream by hydrogenation over a palladium catalyst in a reactive distillation column. Although the content of acetylenic compounds in the top product had only been reduced by approx. 60% and that of 1,2-butadiene only by 32% in the example 1 reported there, as much as 3% of the 1,3-butadiene had been lost by hydrogenation.

In Angew. Cherm. 2005, 117, 2062-2065, Jeroen W. Sprengers et al. report that Pd complex catalysts which have N-heterocyclic ligands as ligands are suitable as catalysts for hydrogenation, in particular for the hydrogenation of 1-phenyl-1-propyne to 1-phenyl-1-propene and 1-phenyl-1-propane.

In the preparation of 2,7-octadienyl derivatives from crack $C_4$ by telomerization according to the prior art, complicated processes, especially with regard to the apparatus complexity, are needed to remove inhibitors such as alkynes from the feedstock mixture. These processes have the disadvantage that a portion of the 1,3-butadiene, especially when it is attempted to get the alkyne content in the feedstock mixture below the detection limit, is lost in the removal of the inhitors. When 1,3-butadiene losses are avoided by dispensing with a substantially full removal of the inhibitors, a lower space-time yield or selectivity in the telomerization or a higher catalyst consumption has to be accepted.

It is therefore an object of the present invention to provide an alternative telomerization process which preferably avoids some or all of the disadvantages of the prior art mentioned.

It has now been found that, surprisingly, addition of hydrogen via a hydrogen source into at least one step of the overall telomerization process can prevent inhibition of the telomerization catalyst, or can reactivate it in the case of inhibition of the catalyst.

The invention accordingly provides a process for telomerizing noncyclic olefins having at least two conjugated double bonds (VI) with at least one nucleophile (VII) using a catalyst containing a metal of group 8 to 10 of the Periodic Table of the Elements, wherein the overall telomerization process includes at least one step in which hydrogen is added via a hydrogen source selected from a gas comprising hydrogen to the process mixture present in this step.

The present invention likewise provides a mixture comprising 2,7-octadienyl derivatives, prepared by the process according to the invention, and to the use of this mixture for preparing 1-octene.

The process according to the invention has the advantage that a very costly and inconvenient removal of all inhibitors, in particular all alkynes, from the feedstock mixture can be dispensed with. In addition to the reduced apparatus complexity, the process also has the advantage that it is also possible to avoid the use of expensive hydrogenation catalyst.

The process according to the invention additionally has the advantage that telomerization catalysts may be dispensed with, since the telomerization catalyst is deactivated distinctly more slowly, if at all.

The process according to the invention also has the advantage that the allenes and cumulenes, i.e. the co mpounds having cumulated double bonds, such as 1,2-butadiene, which constitute an important starting material for organic synthesis, are substantially not destroyed, but rather remain present in the hydrocarbon stream and can be removed after the second process step, that of the telomerization, in the workup of the telomerization product.

The process according to the invention will be described by way of example below, without any intention that the invention, whose scope of protection is evident from the claims and the description, be restricted thereto. The claims themselves also belong to the disclosure content of the present invention. When ranges, general formulae or compound classes are specified below, these are intended not only to incorporate the corresponding ranges or groups of compounds which are mentioned explicitly, but rather all subranges and subgroups of compounds which can be obtained by omitting individual values (ranges) or compounds.

The process according to the invention for telomerizing noncyclic oletins having at least two conjugated double bonds (VI) with at least one nucleophile (VII) using a catalyst comprising a metal of group 8, 9 or 10 of the Periodic Table of Elements has the feature that the overall telomerization process includes at least one step in which hydrogen is added via a hydrogen source selected from a gas comprising hydrogen to the process mixture present in this step. The gas comprising hydrogen can be obtained in situ, for example from hydrazine.

The hydrogen source used may in particular be a hydrogen-containing gas, preferably hydrogen gas alone or in a mixture with gases inert to the telomerization, for example nitrogen, methane or noble gas(es).

Preference is given to adding the hydrogen source as early as the start of the appropriate step. The hydrogen source is preferably fed into the step via an apparatus which is suitable for distributing the hydrogen source in a very fine manner. When the hydrogen source is a gas, the apparatus may, for example, be a mixer nozzle. For particularly good homogenization of the gas in the mixture, it may be advantageous when the pressure in the process step is at least 2 MPa, preferably 4 MPa. When the hydrogen source is present in liquid for, very fine distribution can be achieved, for example, by the use of static mixers.

The feedstocks used maay be the pure noncyclic olefins having conjugated double bonds, mixtures of different such oletins or mixtures of one or more of the olefins mentioned with other hydrocarbons. The feedstock used is preferably a mixture of hydrocarbons which comprises one or more noncyclic olefins, preferably one noncyclic olefin, having at least two conjugated double bonds in a mixmre with other hydrocarbons.

Particularly preferred feedstocks comprise, as noncyclic olefins having conjugated double bonds, 1,3-butadiene and/or isoprene, in each case as a pure substance, mixture of the pure substances or in a mixture of one or both olefins with other hydrocarbons, The feedstocks used are most preferably mixtures which contain over 90% by mass of $C_4$ hydrocarbons and preferably 1,3-butadiene.

Suitable feedstocks for the process according to the invention are more preferably 1,3-butadiene-rich hydrocarbon streams. The hydrocarbon stream used may in particular be a $C_4$ hydrocarbon cut. The hydrocarbon streams may preferably, for example, be mixtures of 1,3-butadiene with other $C_4$ and $C_3$ or $C_5$ hydrocarbons. Such mixtures are obtained, for example, in cracking processes for producing ethylene and propylene, in which refinery gases, naphtha, gas oil, LPG (liquefied petroleum gas), NGL (natural gas liquid), etc. The $C_4$ cuts obtained as a by-product in the processes may, in addition to 1,3-butadiene, comprise monoolefins (1-butene, cis-but-2-ene, trans-but-2-ene, isobutene), saturated hydrocarbons (n-butane, isobutane), acetylenically unsaturated compounds (ethylacetylene (butyne), vinylacetylene (butenyne), methylacetylene (propyne) and alienically unsaturated compounds (mainly 1,2-butadiene)). In addition, these cuts may comprise small amounts of $C_3$ and $C_5$ hydrocarbons. The composition of the $C_4$ cuts is dependent upon the particular cracking process, the operating parameters and the feedstock. The concentrations of the individual components for steamcrackers lie typically within the following ranges:

| Component | % by mass |
| --- | --- |
| 1,3-butadiene | 25-70 |
| 1-butene | 9-25 |
| 2-butenes | 4-20 |
| isobutene | 10-35 |
| n-butane | 0.5-8 |
| isobutane | 0.5-6 |
| Σ acetylenic compnds | 0.05-4 |
| 1,2-butadiene | 0.05-2 |

In the process according to the invention, preference is given to using hydrocarbon mixtures having a 1,3-butadiene content of greater than 35% by mass.

The starting hydrocarbons may frequently comprise traces of oxygen compounds, nitrogen compounds, sulfur compounds, halogen compounds, in particular chlorine compounds and heavy metal compounds, which might be disruptive in the process according to the invention. It is therefore appropriate first to remove these substances. Troublesome compounds may, for example, be carbon dioxide or carbonyl compounds, for example acetone or acetaldehyde.

These impurities can be removed, for example, by scrubbing, in particular with water or aqueous solutions, or by means of adsorbers.

Water scrubbing can partly or fully remove hydrophilic components, for example nitrogen components, from the hydrocarbon mixture. Examples of nitrogen components are acetonitrile or N-methylpyrrolidone (NMP). Oxygen compounds too can also partly be removed by means of a water scrubbing. The water scrubbing can be carried out directly with water or else with aqueous solutions which may comprise, for example, salts, for example $NaHSO_3$ (U.S. Pat. No. 3,682,779, U.S. Pat. No. 3,308,201, U.S. Pat. No. 4,125,568, U.S. Pat. No. 3,336,414 or U.S. Pat. No. 5,122,236).

It may be advantageous when the hydrocarbon mixture, after the water scrubbing, passes through a drying step. The drying may be carried out by processes known in the prior art. In the presence of dissolved water, the druing may be carried out, for example, using a molecular sieve as desiccant or by azeotropic distillation. Free water may be removed by phase separation, for example with a coalescer.

Adsorbers may be used to remove impurities in the trace region. This may be advantageous especially because noble metal catalysts are used in the telomerization step and react even to traces of imnpurities with a distinct decline in actvity. Often, nitrogen or sulfur compounds are removed by means of upstream adsorbers. Examples of usable adsorbents are aluminas, molecular sieves, zeolites, activated carbon or metal-impregnated clay earths (for example U.S. Pat. No. 4,571,445 or WO 02/53685). Adsorbents are sold by various companies, for example Alcoa under the name Selexsorb®, by UOP or by Axens, for example in the product series SAS, MS, AA, TG, TGS or CMCG.

Using the process according to the invention, it is possible in particular to use feedstock mixtures which also contain compounds including allenically unsaturated compounds and or have a content of greater than or equal to 50% by mass (wppm), preferably greater than or equal to 100 ppm by mass, of acetylenically unsaturated compounds. In the process according to the invention, the feedstocks used may preferably be mixtures which comprise noncyclic olefins having conjugated double bonds and contain up to 5% by mass, preferably up to 3% by mass and more preferably up to 1% by mass, of alkynes or acetylenically unsaturated compounds. As a result of the usability of feedstock mixtures which still comprise small residual amounts of acetylenically unsaturated compounds, it is possible to use numerous hydrocarbon mixtures obtained in industry, especially $C_4$ or $C_5$ hydrocarbon mixtures, directly as feedstocks in the process according to the invention for telomerization. Should a distinctly higher content of acetylenically unsaturated compounds be present in a possible feedstock mixture, it may be advantageous to remove at least a portion of the acetylenically unsaturated compounds (alkynes) present from this mixture before use in the telomerization, for example by selective hydrogenation or extraction, so that the feedstock mixture used can then be a mixture which contains from 0 to 5% by mass, preferably from 50 wppm to 3% by mass and more preferably from 100 wppm to 1% by mass, of acetylenically unsaturated compounds. Processes for extraction or selective hydrogenation can be taken from the prior art.

The removal of the acetylenic compounds by extraction has been known for some time and is, as a workup step, an integral part of most plants which obtain 1,3-butadiene from crack $C_4$. A process for extractively remnoving acetylenically unsaturated compounds from crack $C_4$ is described, for example, in *Erdöl und Kohle-Erdgas-Petrochemie vereinigt mit Brennstoffchemie* Vol. 34, No. 8, August 1987, page 343-346. In this process, the polyunsaturated hydrocarbons and the acetylenically unsaturated compounds are removed in a first stage by extractive distillation with aqueous NMP from the monoolefins and saturated hydrocarbons. From the NMP extract, the unsaturated hydrocarbons are removed distillatively. From the hydrocarbon distillate, a second extractive distillation using aqueous NMP removes the acetylenically unsaturated compounds having four carbon atoms. In the workup of crack $C_4$, two further distillations remove pure 1,3-butadiene, and the by-products obtained are methylacetylene and 1,2-butadiene. In the context of the process according to the invention, the multistage process described here may be carried out as a pretreatment for the feedstock mixture, in which case the distillative removal of the 1,2-butadiene can be dispensed with.

Optionally, acetylenic compounds can be removed from a 1,3-butadiene-containing stream using one or more ionic liquid(s), for example as an extractant.

The hydrocarbon streams which are obtained by extraction and contain preferably less than 5% by mass of acetylenic compounds may more preferably be used directly as a feedstock in the process according to the invention.

The partial removal of the acetylenically unsaturated compounds from the hydrocarbon stream to be used by selective hydrogenation of the acetylenically unsaturated compounds in the presence of dienes and monoolefins can be carried out, for exarmple, over copper or palladium catalysts, or over mixed catalysts.

If acetylenically unsaturated compounds are present, the feedstocks used in the process according to the invention, especially when $C_4$ hydrocarbon mixtures comprising 1,3-butadiene are used, comprise acetylenically unsaturated compounds (alkynes) which are preferably selected from vinylacetylene and/or 1-butyne.

When alkynes are present in the feedstock mixture, preference is given to adding via the hydrogen source sufficient hydrogen that the molar ratio of hydrogen to acetylenically unsaturated compounds (alkynes) in the starting mixture is at least 1:1, preferably from 1:1 to 2:1, more preferably from 1:1 to 1.5:1 and most preferably from 1:1 to 1.1:1. A distinct exceedance of these values leads to increasing loss of the noncyclic olefins having conjugated double bonds, for example of 1,3-butadiene. The concentration of the alkyne in the feedstock mixture may be determined continuously or at regular intenrals, for example by gas chromatography.

In the process according to the invention, all catalysts suitable for the telomerization may be used. Preferred catalysts for the telomerization are metal complexes of the metals palladium (Pd), iron (Fe), ruthenium (Ru), osmium (Os), cobalt (Co), rhodium (Rh), iridium (Ir), nickel Ni) or platinum (Pt). The ligands used may, for example, be phosphorus ligands, for example phosphines, phosphinines, phosphinites, phosphonites or phosphites, for example triphenylphosphines or carbene ligands, and it may also be advantageous to use different ligands at the same time. Particular preference is given to using metal-carbene complexes as catalysts.

Very particular preference is given to using palladium compounds, in particular palladium-carbene complexes, as catalysts in the telomerization step. The ligands in the metal complexes used as the catalyst are more preferably trivalent phosphorus compounds or carbenes.

Particular preference is given to using metal complexes as the catalyst which have at least one carbene ligand stabilized by heteroatoms. Examples of such ligands are described, inter alia, in the documeents DE 101 28 144, DE 101 49 348, DE 101 48 722, DE 100 62 577, EP 1 308 157 and WO 01/66248. These documents and in particular the ligands described there are included in the disclosure content of the present application. In addition, the active complex may corprise further ligands. The carbene ligands may be open ligands or cyclic ligands.

The telomerization catalyst used in the process according to the invention is preferably a palladium-carbene complex which has a carbene ligand of the general formula (VIII)

VIII where $R^2$, R", R' and $R^3$ may be the same or different and may each be hydrogen or hydrocarbon groups, where the hydrocarbon groups may be identical or different linears branched or cyclic radicals selected from the group of alkyl radicals having from 1 to 50 carbon atoms. alkenyl radicals having from 2 to 50 carbon atoms, alkynyl radicals having from 2 to 50 carbon atoms and aryl radicals having from 6 to 30 carbon atoms, in which at least one hydrogen atom may be replaced by a functional group, and or $R^2$ and R" and/or R' and $R^3$ are each part of a cyclic system which is the same or different and has a carbon skeleton having from 2 to 20 carbon atoms and a nitrogen atom according to formula VIII, where the carbon atoms of $R^2$ and R" and/or R' and $R^3$ are not counted and where at least one hydrogen atom in the cyclic system may be replaced by a functional group and/or at least one carbon atom of the cyclic system may be replaced by a heteroatom selected from the group consisting of S, P, O and N.

and/or $R^2$ and/or R" and/or R' and or $R^3$ are joined by a bridge composed of from 1 to 20 carbon atoms to a ligand L, where the carbon atoms of the $R^2$, R", R' and $R^3$ radicals are not counted, and L is a further ligand which is an uncharged two-electron donor, part of a cyclic system and/or an anionic ligand, where the functional groups may, for example be selected from the groups —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H and —PO$_3$H$_2$, where the alkyl groups may contain for example, from 1 to 24 carbon atoms, and the aryl groups, for example, from 5 to 24 carbon atoms. The preparation of such ligands can be taken for example, from DE 101 48 722.

In the process according to the invention, the telomerization catalyst used is preferably a palladium-carbene complex which has a carbene ligand of the general formula (VIII) where

$R^2$; $R^3$: are the same or different and are each linear, branched, substituted or unsubstituted, cyclic or alicyclic alkyl groups having from 1 to 24 carbon atoms, or substituted or unsubstituted, mono- or polycyclic aryl groups having from 6 to 24 carbon atoms or mono- or polycyclic, substituted or unsubstituted heterocycle having from 4 to 24 carbon atoms and at least one heteroatom from the group of N, O, S, R', R": are the same or different and are each hydrogen, alkyl, aryl, heteroaryl, —CN, —COOH, —COO-alkyl-, —COO-akyl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H, —PO$_3$H$_2$, where the alkyl groups contain 1-24 carbon atoms and the aryl and heteroaryl groups from 5 to 24 carbon atoms, and the R' and R" radicals may also be part of a bridging aliphatic or aromatic ring.

Very particular preference is given to using carbene ligands which have a 5-membered ring. Ligands which have a 5-membered ring and are used with preference in the process according to the invention are, for example, those of the formulae IX, X, XI and XII

IX

X

XI

XII where $R^2$; $R^3$: are the samne or different and are each linear, branched, substituted or unsubstituted, cyclic or alicyclic alkyl groups having from 1 to 24 carbon atoms, or substituted or unsubstituted, mono- or polycyclic aryl groups having from 6 to 24 carbon atoms or mono- or polycyclic, substituted or unsubstituted heterocycle having from 4 to 24 carbon atoms and at least one heteroatom from the group of N, O, S, $R^4$, $R^5$, $R^6$, $R^7$: are the same or different and are each hydrogen, alkyl, aryl, heteroaryl, —CN, —COOH, —COO-alkyl-, —COO-aryl-, —OCO-akyl-, —OCO-aryl-, —OCOO-alkyl-, —OCOO-aryl-, —CHO, —CO-alkyl-, —CO-aryl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H, —PO$_3$H$_2$, where the alkyl groups contain 1-24 carbon atoms and the aryl and heteroaryl groups from 5 to 24 carbon atoms, and the $R^4$, $R^5$, $R^6$ and $R^7$ radicals may also be part of a bridging aliphatic or aromatic ring.

Examples of carbene ligands which correspond to the general formulae IX or X and complexes which contain such ligands have already been described in the technical literature (W. A. Herrmann, C. Köcher, Angew. Chem. 1997, 109, 2257; Angew. Chem. Int. Ed. Engl. 1997, 36, 2162; V. P. W. Böhm, C. W. K. Gstöttmayr, T. Weskamp, W. A. Herrmann, J. Organomet. Chem, 2000, 595, 186; DE 44 47 066).

The $R^2$ and $R^3$ radicals may in particular be a mono- or polycyclic ring which contains at least one heteroatom selected from the elements nitrogen, oxygen and sulfur, and optionally has further substituents selected from the group of —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, -aryl-, -alkyl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H, —PO$_3$H$_2$. The alkyl groups have from 1 to 24 carbon atoms and the aryl groups from 5 to 24 carbon atoms. In the case that Pd is used as the metal of group 8 to 10 of the Periodic Table, one or both $R^2$ and $R^3$ ligands preferably has/have these definitions.

The $R^2$, $R^3$, $R^4$, $R^5$, $R^6$ and/or $R^7$ radicals may each be the same or different and have at least one substituent from the group of —H, —CN, —COOH, —COO-alkyl, —COO-aryl, —OCO-alkyl, —OCO-aryl, —OCOO-alkyl, —OCOO-aryl, —CHO, —CO-alkyl, —CO-aryl, -aryl, -alkyl, -alkenyl, -allyl, —O-alky, —O-aryl, —NH$_2$, —NH(alkyl), —N(alkyl)$_2$, —NH(aryl), —N(alkyl)$_2$, —F, —Cl, —Br, —I, —OH, —CF$_3$, —NO$_2$, -ferrocenyl, —SO$_3$H, —PO$_3$H$_2$, where the alkyl groups contain from 1 to 24, preferably from 1 to 20, carbon atoms, the alkenpyl groups from 2 to 24 carbon atoms, the allyl groups from 3 to 24 carbon atoms and the mono- or polycyclic aryl groups from 5 to 24 carbon atoms. The $R_4$ to $R_6$ radicals may, for example, be joined covalently to one another via $(CH_2)$ or (CH) groups.

In the case of substituents having acidic hydrogen atoms, the protons may be replaced by metal or ammonium ions.

The $R^2$ and $R^3$ radicals may more preferably be radicals which derive from five- and six-membered heteroalkanes, heteroalkenes and heteroaromatics, such as 1,4-dioxane, morpholine, γ-pyran, pyridine, pyrimidine, pyrazine, pyrrole, furan, thiophene, pyrazole, imidazole, thiazole and oxazole. The table 1 which follows reproduces specific examples of such $R^2$ and $R^3$ radicals. In this table, ~ indicates in each case the point of attachment to the five-membered heterocyclic ring or to the compound of the formula VIII.

TABLE 1

Examples of possible $R^2$ or $R^3$ radicals

A-1

A-2

A-3

A-19

A-4

A-5

A-6

TABLE 1-continued

Examples of possible $R^2$ or $R^3$ radicals

A-7

A-8

A-9

A-10

A-11

A-12

A-13

A-14

A-15

TABLE 1-continued

Examples of possible R² or R³ radicals

In the context of this invention, carbene ligands are understood to mean both free carbenes which can function as a ligand and carbenes coordinated to metal.

The catalyst metal, in particular the palladium used as the catalyst metal, from which the active catalyst is formed under reaction conditions can be introduced into the process in different ways.

The metal (palladium) can be introduced into the process a) as a metal-carbene complex (palladium-carbene complex), in which case the metal (palladium) is preferably in the (II) or (0) oxidation states, or b) in the form of metal precursors (palladium precursors) from which the catalysts are formed in situ.

a)

Examples are palladium(0)-carbene-olefin complexes, palladium(0)-dicarbene complexes and palladium(II)-dicarbene complexes, palladium(0)-carbene-1,6-diene complexes. The 1,6-diene may, for example, be diallylamine, 1,1'-divinyltetramethyldisiloxane, 2,7-octadienyl ethers or 2,7-octadienyl amines. Further examples are shown by the following formulae I-a to I-e.

-continued

I-f

I-g

I-h

I-i

I-j

-continued

I-k

I-l

The carbene complexes of palladium can be prepared in a wide variety of ways. A simple route is, for example, the addition of carbene ligands or the exchange of ligands on palladium complexes for carbene ligands. For example, the complexes I-f to I-i are obtainable by exchange of the phosphorus ligands of the bis(tri-o-tolylphosphine)palladium(0) complex (T. Weskamp, W. A. Herrmann, *J. Organomet. Chem.* 2000, 595, 186).

I-f $R^2 = R^3$ = Mesityl
I-g $R^2 = R^3$ = c-Hexyl
I-h $R^2 = R^3$ = t-Butyl
I-i $R^2 = R^3$ = i-Propyl b)

The palladium precursors used may, for example, be palladium(II) acetate, palladium(II) choride, palladium(I) bromide, lithium tetrachloropalladate, palladium(II) acetylacetonate, palladium(0)-dibenzylideneacetone complexes, palladium(II) propionate, bisacetointrile-palladium(II) chloride, bistriphenylphosphinepalladium(II) dichloride, bisbenzortrile-palladium(II) chloride, bis(th-o-tolylphosphine)palladium(0) and urther palladium(0) and palladium(II) complexes.

The carbenes of the general formulae IX and X may be used in the for of free carbenes or as metal complexes, or are obtained in situ from carbene precursors.

Suitable carbene precursors are, for example, salts of the carbenes of the general formulae XIII and XIV, where $R^2$, $R^3$, $R^4$, $R^5$, $R^6$, $R^7$ are each as defined in formulae IX and X, and Y is a singly charged anionic group or, in accordance with the stoichiometry, a fraction of a multiply charged anionic group.

Examples of Y are halides, hydrogensulfate, sulfate, alkylsulfates, anylsulfates borates, hydrogencarbonate, carbonate, alkylcarboxylates, arylcarboxylates.

The corresponding carbenes can be released from the salts of the carbenes, for example, by reacting with a base.

The concentration of the catalyst, reported formally in ppm (by mass) of catalyst metal, in particular palladium metal based on the total mass, in the process according to the invention is preferably from 0.01 ppm to 1000 ppm, preferably from 0.5 to 100 ppm more preferably from 1 to 50 ppm. The ratio [mol/mol] of ligand, preferably carbene, to metal, in particular the ratio of carbene to Pd, in the reaction mixture is preferably from 0.01:1 to 250:1, preferably from 1:1 to 100:1, more preferably from 1:1 to 50:1. In addition to the carbene ligands, further ligands, for example phosphorus ligands, e.g. tiphenylphosphine, may be present in the reaction mixture.

The nucleophiles (VII) used are preferably compounds of the general formulae $$R^{1a}\text{—O—H} \tag{VIIa}$$

or $$(R^{1a})(R^{1b})N\text{—H} \tag{VIIb}$$

or $$R^{1a}\text{—COOH} \tag{VIIc}$$

in which $R^{1a}$ and $R^{1b}$ are each independently selected from hydrogen a linear branched or cyclic $C_1$ to $C_{22}$-alkyl group, -alkenyl group or -alkynyl group, a $C_5$ to $C_{18}$-aryl group or a —CO-alkyl-$(C_1$-$C_8)$ group or a —CO-aryl-$(C_5$-$C_{10})$ group, where these groups may contain substituents selected from the group of —CN, —COOH, —COO-alkyl-$(C_1$-$C_8)$, —CO-alkyl-$(C_1$-$C_8)$, -aryl-$(C_5$-$C_{10})$, —COO-aryl-$(C_6$-$C_{10})$, —CO-aryl-$(C_6$-$C_{10})$, —O-alkyl-$(C_1$-$C_8)$, —O—CO-alkyl-$(C_1$-$C_8)$, —N-alkyl$_2$-$(C_1$-$C_8)$, —CHO, —SO$_3$H, —NH$_2$, —F, —Cl, —OH, —CF$_3$ and —NO$_2$, and where the $R^{1a}$ and $R^{1b}$ radicals may be joined together via covalent bonds. The nucleophiles used are preferably compounds in which the $R^{1a}$ and optionally $R^{1b}$ radicals are each hydrogen, methyl, ethyl, n-propyl, isopropyl, tert-butyl, n-butyl sec-butyl, pentyl, hexyl, heptyl, octyl, octenyl, octadienyl, isononyl, 2-ethylhexyl, n-nonyl, phenyl, m-, o- or p-methylphenyl, naphthyl, 2,4-di-tert-butylphenyl, 2,6-di-tert-butylmethylphenyl, hydrogencarbonyl, methylcarbonyl, ethylcarbonyl, propylcarbonyl or phenylcarbonyl.

The nucleophiles (VII) used are more preferably water, alcohols, phenols, polyols, carboxylic acids, ammonia and/or primary or secondary amines. These are especially:
water, ammonia,
monoalcohols and phenols, for example methanol, ethanol n-propanol, isopropanol, allyl alcohol, n-butanol, i-butanol, octanol, 2-ethylhexanol, isononanol, benzyl alcohol, cyclohexanol, cyclopentanol or 2,7-octadien-1-ol, phenol,
dialcohols, for example ethylene glycol, 1,2-propanediol, 1,3-propanediol, 1,4-butanediol, 1,2-butanediol, 2,3-butanediol and 1,3-butanediol
hydroxyl compounds, for example α-hydroxyacetic esters,
primary amines, for example methylamine, ethylamine, propylarrine, butylarnine, octylamine, 2,7-octadienylamine, dodecylamine, ethylenediamrine or hexaethylene-diamine,
secondary amines such as dimethylamine, diethylamine, N-methylaniline, bis(2,7-octadienyl)amine, dicyclohexylamine, methylcyclohexylamine, pyrrolidine, piperidine, morpholine, piperazine or hexamethyleneimine or
carboxylic acids such as formic acid, acetic acid, propanoic acid, butenoic acid, isobutenoic acid, benzoic acid, 1,2-benzenedicarboxylic acid (phthalic acid).

The nucleophiles (VII) used in the telomerization step are most preferably methanol, ethanol, 2-ethylhexanol, octanol, octenol, octadienol, isopropanol, n-propanol, isobutanol, n-butanol, isononanol formic acid, acetic acid propionic acid, n-butanoic acid, isobutanoic acid, benzoic acid, phthalic acid, phenol, dimethylamine, methylamine, ammonia and/or water. Advantageously, the nucleophile used is methanol.

Nucleophiles which can themselves be obtained via a telomerization reaction can be used directly or else formed in situ. For example, 2,7-octadien-1-ol can be formed in situ from water and butadiene in the presence of the telomerization catalyst, 2,7-octadienylamine from ammonia and 1,3-butadiene, etc.

For the ratio of nucleophile to the starting olefin having at least two conjugated double bonds in the telomerization reaction, the number of active hydrogen atoms in the telogen has to be taken into account. For example, methanol has one active hydrogen atom, ethylene glycol has two, methylamine has two, etc.

Per mole of active hydrogen atom of the nucleophile which can react with the starting olefin, preference is given to using from 0.001 mol to 10 mol of starting olefin in the telomerization reaction. In a reaction with a liquid phase, particular preference is given to a ratio of from 0.1 mol to 2 mol of starting olefin per mole or active hydrogen.

It may be advantageous when the process according to the invention is carried out in the presence of a solvent. The solvents used for the telomerization reaction may be the nucleophile used when it is present in liquid form under reaction conditions, and/or inert organic solvents. Preference is given to the addition of solvents when nucleophiles are used which are present in the form of solids under reaction conditions, or in the case of products that would be obtained in the form of solids under the reaction conditions. Suitable solvents include aliphatic, cycloaliphatic and aromatic hydrocarbons, for example $C_3$-$C_{20}$-alkanes, mixtures of lower alkanes ($C_3$-$C_{20}$), cyclohexane, cyclooctane, ethylcyclohexane, alkenes and polyenes, vinylcyclohexene, 1,3,7-octatriene, the $C_4$ hydrocarbons from crack C$_4$ cuts, benzene, toluene and xylene; polar solvents, for example tertiary and secondary alcohols, amides, for example acetamide, dimethylacetamide and dimethylformamide, nitriles, for example acetonitrile and benzonitrile, ketones, for example acetone, methyl isobutyl ketone and diethyl ketone, carboxylic esters, for example ethyl acetate, ethers, for example dipropyl ether, diethyl ether, dimethyl ether, methyl octyl ether, methyl tert-butyl ether, ethyl tert-butyl ether 3-ethoxyoctane, dioxane, tetrahydrofuran, anisole, alkyl and aryl ethers of ethylene glycol, diethylene glycol, triethylene glycol, tetraethylene glycol, polyethylene glycol, propylene glycol, dipropylene glycol, tripropylene glycol and polypropylene glycol, and other polar solvents, for example sulfolane, dimethyl sulfoxide, ethylene carbonate, propylene carbonate and water. It is also possible to use ionic liquids, for example imidazolium or pyridinium salts, as solvents. The solvents may be used alone or as mixtures of different solvents.

The temperature at which the telomerization reaction is performed is preferably in the range from 10 to 180° C., preferably in the range from 30 to 120° C. and more preferably in the range from 40 to 100° C. The reaction pressure is preferably from 1 to 300 bar, preferably from 1 to 120 bar, more preferably from 1 to 64 bar and most preferably from 1 to 20 bar.

It is often advantageous to carry out the telomerization reaction in the presence of bases. Preference is given to using basic components having a pK$_b$ of less than 7, in particular compounds selected from the group of the amines, alkoxides, phenoxides, alkali metal salts or alkaline earth metal salts.

Suitable basic components are, for example, amines such as trialkylamines which may be alicyclic or/and open-chain, amides, alkali metal or/and alkaline earth metal salts of aliphatic or/and aromatic carboxylic acids, such as acetates, propionates, benzoates or corresponding carbonates, hydrogencarbonates, alkoxides of alkali elements and/or alkaline earth elements, phosphates, hydrogenphosphates or/and hydroxides, preferably of lithium, sodium, potassium calcium, magnesium, cesium, ammonium and phosphonium compounds. Preference is given as an additive to hydroxides of alkali metal and alkaline earth metal elements and to metal salts of the nucleophile according to the general formulae III, IV or V.

Preference is given to using from 0.01 mol % to 10 mol % of the basic components (based on the starting olefin), preferably from 0.1 mol % to 5 mol % and most preferably from 0.2 mol % to 1 mol %.

The telomerization may be operated continuously or batchwise and is not restricted to the use of particular reactor types. Examples of reactors in which the reaction can be carried out are stirred tank reactor, stirred tank batteries, flow tubes and loop reactors. Combinations of different reactors are also possible, for example a stirred tank reactor with downstream flow tube.

In order to obtain a high space-time yield, the telomerization may preferably not be carried out up to the full conversion of the starting olefin. This is the case especially when the starting olefin is 1,3-butadiene. In this case, preference is given to restricting the conversion to not more than 95%, more preferably to 88%.

The inventive addition of hydrogen via a hydrogen source to a process mixture present in one step may be effected in one or more steps. When the telomerization process according to the invention has only one step, i.e. the telomerization reaction itself, the hydrogen is of course added by addition of the hydrogen source to this step. The process according to the invention preferably includes one or more further step(s). Such steps may, for example, be a step for removing the catalyst and optionally a step for recycling the catalyst into the reactor. The hydrogen source is preferably added to the overall telomerization process in the reaction step. The addition of hydrogen via the hydrogen source in the reaction step has the advantage that the inhibition of the telomerization can be prevented by acetylenically unsaturated compounds directly in the reaction mixture. However, a disadvantage of the addition of the hydrogen in the reaction step may be that reactants or products can be hydrogenated to undesired by-products, which can result in yield losses. This is the case especially when the telomerization is carried out with an excess of hydrogen in comparison to the acetylenically unsaturated compounds present.

When the overall telomerization process has a catalyst recycling step, the hydrogen source is added to the overall telomerization process preferably in the catalyst recycling step. The addition of the hydrogen source to the catalyst recycling has the advantage that the product and also the reactant have been removed very substantially from the catalyst in a preceding step, and the hydrogen added via the hydrogen source thus does not hydrogenate valuable reactant or product to undesired by-products and thus does not reduce the yield. It may be advantageous when the hydrogen source is added both to the reaction step and to the catalyst recycling step.

The process according to the invention may be used in particular for preparing, from a 1,3-butadiene-containing hydrocarbon stream, a compound of the formula II

II in which X is an OR$^{1a}$ or NR$^{1a}$R$^{1b}$ radical, where R$^{1a}$ and R$^{1b}$ are each independently selected from hydrogen, a linear, branched or cyclic C$_1$ to C$_{22}$-alkyl group, an alkenyl group, an alkynyl group, a C$_5$ to C$_{18}$ aryl group or a —CO-alkyl-(C$_1$-C$_8$) group or a —CO-aryl-(C$_5$-C$_{10}$) group, where these groups may contain substituents selected from the group of —CN, —COOH, —COO-alkyl-(C$_1$-C$_8$), —CO-alkyl-(C$_1$-C$_8$), -aryl-(C$_5$-C$_{10}$), —COO-aryl-(C$_6$-C$_{10}$), —CO-aryl-(C$_6$-C$_{10}$), —O-alkyl-(C$_1$-C$_8$), —O—CO-alkyl-(C$_1$-C$_8$), —N-alkyl$_2$-(C$_1$-C$_8$) —CHO, —SO$_3$H, —NH$_2$, —F, —Cl, —OH, —CF$_3$, —NO$_2$, and where the R$^{1a}$ and R$^{1b}$ radicals may be joined together via covalent bonds.

Using the process according to the invention, it is possible in particular to prepare compounds of the formula IIIa or IIIb, IIIa IIIb by reacting 1,3-butadiene with a nucleophile (VII) of the formulae VIIa, VIIb or VIIc R$^{1a}$—O—H (VIIa)

(R$^{1a}$)(R$^{1b}$)N—H (VIIb)

R$^{1a}$—COOH (VIIc)

where R$^{1a}$ and R$^{1b}$ are each as defined above.

Particular preference is given to using the process according to the invention to prepare compounds of the formula II in which X is $OR^{1a}$ or $NR^{1a}R^{1b}$, where $R^{1a}$ is H, methyl, ethyl, n-propyl, isopropyl, tert-butyl, n-butyl, sec-butyl, pentyl, hexyl, heptyl, octyl, octenyl, octadienyl, isononyl, 2-ethylhexyl, n-nonyl, phenyl, m-, o- or p-methylphenyl, naphthyl, 2,4-di-tert-butylphenyl, 2,6-di-tert-butylmethylphenyl hydrogencarbonyl, methylcarbonyl, ethylcarbonyl, propylcarbonyl or phenylcarbonyl and/or $R^{1b}$ is H, methyl, ethyl, n-propyl, isopropyl, tert-butyl, n-butyl, sec-butyl, pentyl, hexyl, heptyl, octyl, octenyl, octadienyl, isononyl, 2-ethylhexyl, n-nonyl, phenyl, m-, o- or p-methylphenyl, naptyl, 2,4-di-tert-butylphenyl, 2,6-di-tert-butylmethylphenyl, hydrogencarbonyl, methylcarbonyl, ethylcarbonyl, propylcarbonyl or phenylcarbonyl. Very particular preference is given to using the process according to the invention to prepare a compound of the formula IIIa where $R^{1a}$=hydrogen, methyl, ethyl, phenyl or methylcarbonyl. The compounds of the formulae IIIa and IIIb may be present either in the cis or in the trans form.

The effluent from the telomerization reaction step may for example, comprise mainly the telomerization product, by-products, "inert hydrocarbons", residual amounts of starting olefin, residual amounts of nucleophile and catalyst system (catalyst metal, ligands and optionally bases, etc.) or subsequent products thereof and any added solvents, or consist thereof The effluent from the telomerization reaction step may be separated quite generally by known industrial processes, in particular by thermal separating processes, for example distillation or extraction. For example, a distillative separation can be effected into the following fractions:

- a $C_4$ fraction which conmprises n-butane, isobutane, 1-butene, 2-butenes, isobutene, 1,3-butadiene 1,2-butadiene and, if appropriate, all or some of the nucleophile,
- a fraction comprising the target product (2,7-octadienyl dervative),
- a fraction comprising the by-product and/or
- a fraction comprising the catalyst and
- if appropriate, a fraction comprising the nucleophile and/or
- if appropriate a solvent fraction.

The fraction comprising the nucleophile, the fraction comprising the solvent and the fraction comprising the catalyst may each be recycled fully or partly together or separately into the reaction step, or else be fed to a workup. Preference is given to recycling these fractions into the reaction step.

However the separation may also be carried out in such a way that only two fractions are obtained. In this case, one fraction comprises the substantial portion of the target product and the second fraction comprises the substantial portion of the catalyst used. The catalyst-containing fraction is in turn recycled fully or partly into the reaction step.

The target product is used as such or serves as a precursor for other substances. For example, 1-octene can be prepared from the 1-methoxyoctadi-2,7-ene target product by hydrogenating the two double bonds and subsequently eliminating methanol. By means of the process according to the invention, it is thus possible to prepare mixtures comprising 1-methoxyoctadi-2,7-ene. These mixtures can then be used to prepare 1-octene.

When the nucleophile used in the telomerization is methanol or ethanol, the use of $C_4$ hydrocarbon streams as the starting stream (1,3-butadiene as the starting olefin) gives rise to the option of not removing the nucleophile from the reaction product. Instead, the effluent of the hydrogenation of the target product (e.g. 1-methoxyoctadi-2,7-ene) can be sent directly to an etherification in which the alcohol used as a nucleophile is reacted with the isobutene present in the $C_4$ stream to give methyl tert-butyl ether or ethyl tert-butyl ether. This reaction too is effected by processes known in industry, usually under catalysis of ion exchangers. For full conversion of the isobutene, alcohol has to be added additionally in some cases.

Figure 1:
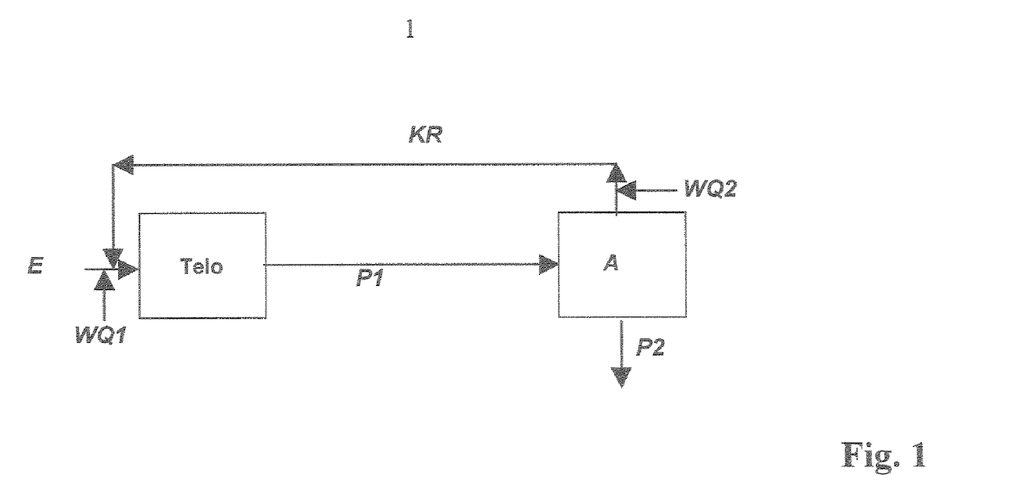

The invention is illustrated in detail with reference to the figure FIG. 1, without any intention that the invention be restricted to the embodiment shown in FIG. 1. FIG. 1 is a schematic illustration of one possible embodiment of the process according to the invention. The overall telomerization process shown here has three steps: one telomenzation reaction step (Telo), one removal step (A) and one catalyst recycling step (KR). In the reaction step (Telo), a reactant stream is conducted together with the catalyst recycle stream (KR) and optionally a hydrogen source (WQ1). The reaction mixture obtained as the reaction product (P1) is conducted into the following step (A), in which the catalyst and optionally a solvent are removed from the remaining constituents of the reaction mixture. The product mixture (P2) freed of catalyst may be sent to a further workup. The removed catalyst is sent back to the reactant stream via the catalyst recycling (KR). In the catalyst recycling, a hydrogen source (WQ2) may also be added to the catalyst stream. When the process according to the invention is carried out it is possible for a hydrogen source to be fed into one or more steps of the overall telomerization process either via WQ1 or WQ2 or else WQ1 and WQ2. It is self-evident that, when the process is carried out, it is possible that further apparatus, for example pumps and valves, etc. or means, for example, of discharging a portion of the used catalyst and/or of adding fresh catalyst, may be or have to be present, but are not sheon in this scheme in FIG. 1.

The examples which follow are intended to illustrate the invention in detail without restricting the scope of protection which is evident from the description and the claims.

EXAMPLES

Example 1

Telomerization in the Absence of Alkynes

In a 100 ml Schlenk tube, 55.9 mg (0.18 mmol) of palladium acetylacetonate and 0.390 g (0.75 mmol) of 1,3-bis(2,4,6-trimethylphenyl)imidazolium-o-cresoxide-o-cresol were dissolved under protective gas in 51.2 g (1.59 mol) of methanol. In a 3-liter autoclave from Büchi, 6.72 g (0.06 mol) of o-cresol, heated to 40° C. in a water vat, and 3.47 g (0.06 mol) of sodium methoxide were dissolved in 115 g (3.59 mol) of methanol and in 100 g (0.52 mol) of tripropylene glycol. Subsequently, with the aid of a pressurized gas canister, 536 g of a $C_4$ hydrocarbon mixture were injected into the autoclave (determination of amounts by a loss of mass in the $C_4$ supply bottle). The autoclave was heated to reaction temperature (80° C.) with stirring, the palladium-containing solution was introduced in one portion into the autoclave contents and the reaction was monitored with the aid of an online gas chromatograph. The reaction time was 14 h. The hydrocarbon mixture obtained was an alkyne-free $C_4$ hydrocarbon mixture having 42.61% by mass of 1,3-butadiene, 1.77% by mass of isobutane 7.05% by mass of n-butane, 5.14% by mass of trans-butene, 15.05% by mass of 1-butene, 24.80% by mass of isobutene, 3.8% by mass of cis-butene (no alkynes were detectable).

GC Analysis:

GC (1st column: DB-WAX/Al$_2$O$_3$, 2nd column: DB-Wax/HP-5MS; stating temperature: 50° C., maximum temperature: 200° C., starting time: 1 min, equilibration time: 3 min; temperature program: from 50° C. at 15° C. min$^{-1}$ to 200° C., run time: 11 min; inj.: 220° C., const. flow rate). Retention time [tR](C$_4$ hydrocarbons)=2762 min, tR(methanol)=3152 min, tR(1,7-octadiene)=3866 min, tR(trans-1,6-octadiene)=3958 min, tR(cis-1,6-octadiene)=4030 min, tR(cis-1,3,7-octatriene)=4291 min, tR(trans-1,3,7-octatriene)=4292 min, tR(vinylcyclohexene)=4448 min, tR(i-butane)=4552 min, tR(n-butane)=4822 min, tR(3-MODE)=5523 min, tR(trans-butene)=6116 min, tR(1-b-utene)=6240 min, tR(i-butene)=6412 min, tR(cis-butene)=6616 min, tR(1-MODE)=6650 min, tR(1,2-butadiene)=6900 min, tR(1,3-butadiene)=7526 min.

2,7-octadien-1-yl methyl ether (=1-MODE)
1,7-octadien-3-yl ethyl ether (=3-MODE)

Example 2

Telomerization in the Presence of 2273 ppm by Mass of Acetylenes (Comparative Experiments)

In a 100 ml Schlenk tube, 56.2 mg (0.18 mmol) of palladium acetylacetonate and 0.395 g (0.76 mmol) of 1,3-bis(2,4,6-trimethylphenyl)imidazolium-o-cresoxide-o-cresol were dissolved under protective gas in 51.2 g (1.59 mol) of methanol. In a 3-liter autoclave from Büchi, 6.80 g (0.062 mol) of o-cresol, heated to 40° C. in a water vat, and 3.80 g (0.07 mol) of sodiunm methoxide were dissolved in 115.1 g (3.591 mol) of methanol and in 101.1 g (0.52 mol) of tripropylene glycol. Subsequently, with the aid of a pressurized gas canister, 573 g of a C$_4$ hydrocarbon mixture were injected into the autoclave (determination of amounts by a loss of mass in the C$_4$ supply bottle). The autoclave was heated to reaction temperature (80° C.) with stiring, the palladium-containing solution was introduced into the autoclave contents and the reaction was monitored with the aid of an online gas chromatograph. The reaction time was 14 h. GC (1st column: DB-WAX/Al$_2$O$_3$, 2nd column: DB-Wax/HP-5MS; starting temperature: 50° C., maximum termperature: 200° C., starting time: 1 min, equilibration time: 3 min; temperature program: from 50° C. at 15° C. min$^{-1}$ to 200° C., run time: 11 min; inj.: 220° C., const. flow rate), tR(C$_4$ hydrocarbons)=2762 min, tR(methanol)=3152 min, tR(1,7-octadiene)=3866 min, tR(trans-1,6-octadiene)=3958 min, tR(cis-1,6-octadiene)=4030 min, tR(cis-1,3,7-octatriene)=4291 min, tR(trans-1,3,7-octatriene)=4292 min, tR(vinylcyclohexene)=4448 min, tR(i-butane)=4552 min, tR(n-butane)=4822 min, tR(3-MODE)=5523 min, tR(trans-butene)=6116 min, tR(1-butene)=6240 min, tR(i-butene)=6412 min, tR(cis-butene)=6616 min, tR(1-MODE)=6650 min, tR(1,2-butadiene)=6900 min, tR(1,3-butadiene)=7526 min.

2,7-octadien-1-yl methyl ether (=1-MODE)
1,7-octadien-3-yl methyl ether (=3-MODE)

In the inventive example, a C$_4$ hydrocarbon mixture having 45.39% by mass of 1,3-butadiene, 1.46% by mass of isobutane, 4.61% by mass of n-butane, 5.20% by mass of trans-butene, 15.22% by mass of 1-butene, 23.85% by mass of cis-butene, 0.1866% by mass of vinylacetylene and 0.0407% by mass of 1-butyne was used.

Example 3

Telomerization with Addition of Water (in Accordance with the Invention)

In a 100 ml Schlenk tube, 55 mg (0.181 mmol) of palladium acetylacetonate and 0.384 g (0.96 mmol) of 1,3-bis(2,4,6-trimethylphenyl)imidazolium-o-cresoxide-o-cresol were dissolved under protective gas in 50.2 g (1.57 mol) of methanol. In a 3-liter autoclave from Büchi, 6.98 g (0.064 mol) of o-cresol, heated to 40° C. in a water vat, and 3.95 g (0.070 mol) of sodium methoxide were dissolved in 115.2 g (3.59 mol) of methanol and in 100.7 g (0.52 mol) of tripropylene glycol. Subsequently, with the aid of a pressurized gas canister, 526 g of a C$_4$ hydrocarbon mixture were injected into the autoclave (determination of amounts by a loss of mass in the C$_4$ supply bottle).

Without heating the reaction mixture, in each case 0.1 MPa of hydrogen was injected after 1 min, 3 h 2 min, 22 h 35 min, 25 h 10 min, 27 h 11 min, 29 h 50 min and 49 h 10 min, and the concentration of the alkynves in the gaseous C$_4$ sample was measured by means of a gas chromatograph (GC). After 52 h 45 min, the autoclave was heated to reaction temperature (80° C.) with stirring. The reaction time at 80° C. was 8.5 h.

GC (1st column: DB-WAX/Al$_2$O$_3$, 2nd column: DB-Wax/HP-5MS; starting temperature: 50° C., maximum temperature: 200° C., starting time: 1 min, equilibration time: 3 min; temperature program: from 50° C. at 15° C. min$^{-1}$ to 200° C., run time: 11 min; inj.: 220° C., const. flow rate), tR(C$_4$ hydrocarbons)=2762 min, tR(methanol)=3152 min, tR(1,7-octadiene)=3866 min, tR(trans-1,6-octadiene)=3958 min, tR(cis-1,6-octadiene)=4030 min, tR(cis-1,3,7-octatriene)=4291 min, tR(trans-1,3,7-octatriene)=4292 min, tR(vinylcyclohexene)=4448 min, tR(i-butane)=4552 min, tR(n-butane)=4822 min, tR(3-MODE)=5523 min, tR(trans-butene)=6116 min, tR(1-butene)=6240 min, tR(i-butene)=6412 min, tR(cis-butene)=6616 min, tR(1-MODE)=6650 min, tR(1,2-butadiene)=6900 min, tR(1,3-butadiene)=7526 min.

2,7-octadien-1-yl methyl ether (=1-MODE)
1,7-octadien-3-yl methyl ether (=3-MODE)

In the inventive example, a C$_4$ hydrocarbon mixture comprising 43.48% by mass of 1,3-butadiene, 3.58% by mass of isobutane, 5.69% by mass of n-butane, 4.00% by mass of trans-butene, 14.78% by mass of 1-butene, 24.9% by mass of isobutene, 2.56% by mass of cis-butene and 0.005% by mass of propyne, 0.6299% by mass of vinylacetylene and 0.1058% by mass of 1-butyne (7407 ppm by mass of alkkynes) was used.

Example 4

Telomerization with Addition of Water (in Accordance with the Invention)

In a 100 ml Schlenk tube, 57.6 mg (0.189 mmol) of palladium acetylacetonate and 0.399 g (0.76 mmol) of 1,3-bis(2,4,6-trimethylphenyl)imidazolium-o-cresoxide-o-cresol were dissolved under protective gas in 51.3 g (1.60 mol) of methanol. In a 3-liter autoclave from Büchi, 6.90 g (0.064 mol) of o-cresol, heated to 40° C. in a water vat, and 3.80 g (0.070 mol) of sodium methoxide were dissolved in 115.1 g (3.59 mol) of methanol and in 102 g (0.53 mol) of tripropylene glycol. Subsequently, with the aid of a pressurized gas canister, 495 g of a C$_4$ hydrocarbon mixture were injected into the autoclave (determination of amounts by a loss of mass in the C$_4$ supply botle). The autoclave was heated to reaction temperature (80° C.) with stirring and the palladium-containing solution was introduced into the autoclave contents. Next, 1.4 MPa of hydrogen were injected. The reaction was monitored with the aid of an online gas chromatograph. The reaction time was 14 h.

GC (1st column: DB-WAX/Al$_2$O$_3$, 2nd column: DB-Vax/HP-5MS; starting temperature: 50° C., maximum temperature: 200° C., starting time: 1 min, equilibration time: 3 min; temperature program: from 50° C. at 15° C. min$^{-1}$ to 200° C., run time: 11 min; inj.: 220° C., const. flow rate, tR(C$_4$ hydrocarbons)=2762 min, tR(methanol)=3152 min, tR(1,7-octadiene)=3866 min, tR(trans-1,6-octadiene)=3958 min, tR(cis-1,6-octadiene)=4030 min, tR(cis-1,3,7-octatriene)=4291 min, tR(trans-1,3,7-octatriene)=4292 min, tR(vinylcyclohexene)=4448 min, tR(i-butane)=4552 min, tR(n-butane)=4822 min, tR(3-MODE)=5523 min, tR(trans-butene)=6116 min, tR(1-butene)=6240 min, tR(i-butene)=6412 min, tR(cis-butene)=6616 min, tR(1-MODE)=6650 min, tR(1,2-butadiene)=6900 min, tR(1,3-butadiene)=7526 min.

2,7-octadien-1-yl methyl ether (=1-MODE)
1,7-octadien-3-yl methyl ether (=3-MODE)

In the inventive example, a C$_4$ hydrocarbon mixture comprising 44.69% by mass of 1,3-butadiene, 2.56% by mass of isobutane, 4.82% by mass of n-butane, 3.96% by mass of trans-butene, 15.50% by mass of 1-butene, 24.68% by mass of isobutene, 2.76% by mass of cis-butene and 0.0415% by mass of propyne, 0.4609% by mass of vinylacetylene and 0.2328% by mass of 1-butyne (7350 ppm by mass of alkynes).

though it was not possible to fully restore the reaction rate of example 1. A side reaction observed is hydrogenation of butadiene to the butenes.

It is suspected that the particularly high conversion at the start of the reaction in example 3 in comparison to examples 1 and 4 can be attributed to the aikynes which deactivate the catalyst already having been removed fully by hydrogenation before the start of the actual reaction in the presence of the telomerization catalyst and any deactivated catalyst having been reactivated. It is suspected that the reason for the greater yield of MODE in example 3 in comparison to example 4 is that the single addition of hydrogen according to example 4 has resulted in the presence of such a great excess of hydrogen in the reaction mixture that the hydrogenation of butadiene to butenes proceeds to an increased extent as a competing reaction to the hydrogenation of the alkynes. A further reason for the amount of MODE being greater in example 3 for comnparable residence time/reaction time might be that the regeneration does not proceed very rapidly, but the hydrogenation and telomerization do proceed in parallel, so that a smaller amount of active catalyst is available. The advantage of the embodiments of the process according to the invention according to example 4 lies in the possibility of dispensing with a time-consuming step of prehydrogenation or preregeneration as carried out in example 3.

TABLE 2

Comparison of the results of examples 1 to 4

| Example 1 | | | | Example 2 | | | | Example 3 | | | | Example 4 | | | |
|---|---|---|---|---|---|---|---|---|---|---|---|---|---|---|---|
| Time min | Conversion % | Sel. MODE %* | Yield % MODE | Time min | Conversion % | Sel. MODE %* | Yield % MODE | Time min | Conversion % | Sel. MODE %* | Yield % MODE | Time min | Conversion % | Sel. MODE %* | Yield % MODE |
| 0 | 0.67 | 100 | 0.5 | 0 | 2.6 | 100 | 2.6 | 0 | 3.62 | 100 | 3.2 | 0 | 2.57 | 96.80 | 2.6 |
| 140 | 65.22 | 96.53 | 62.0 | 140 | 1.53 | 90.48 | 1.4 | 140 | 84.07 | 96.59 | 75.3 | 140 | 37.45 | 96.42 | 26.0 |
| 350 | 97.71 | 96.37 | 93.3 | 380 | 1.75 | 82.18 | 1.4 | 330 | 98.0 | 96.27 | 88.3 | 350 | 96.22 | 96.83 | 74.8 |
| 710 | 99.33 | 95.89 | 94.4 | 800 | 2.18 | 72.13 | 1.6 | 510 | 98.64 | 95.82 | 89.1 | 770 | 99.06 | 95.76 | 76.1 |

*Sel. MODE = Selectivity for MODE among C$_8$ products
Yield % MODE = mol of MODE (from GC) per mole of butadiene in the reactant × 2 × 100%

As can be seen readily by the comparison of examples 1 and 2, the presence of alkynes in the C$_4$ hydrocarbon mixture used leads to inhibition of the catalyst, so that telomerization does not take place under otherwise identical conditions. In example 3, the starting material is a C$_4$ hydrocarbon mixture which has an even greater proportion of acetylenes. Hydrogen is added regularly to the reaction mixture. After approx 37 hours, a slow start to the reaction can be observed even at low temperature. After a subsequent temperature increase, spite of the presence of alkynes in the starting C$_4$ hydrocarbon mixture, telomerization can be observed. The inventive addition of a hydrogen source to the reaction mixture was able to reactivate the inhibited catalyst.

Example 4 also demonstrates that presence of hydrogen in the telomerization reaction can neutralize the inhibiting action of the alkynes. In example 4, the hydrogen is metered in shortly before the start of the reaction and the mixture is immediately heated to 80° C. In spite of the higher amount of alkyne compared to example 2, a high degree of product formation can be observed in the presence of hydrogen, even

What is claimed is:

1. A telomerization process, comprising:
   telomerizing a feedstock which comprises noncyclic olefins having at least two conjugated double bonds (VI) with at least one nucleophile (VII) using a catalyst containing a metal of group 8, 9 or 10 of the Periodic Table of the Elements, and
   at least one step of adding hydrogen to a reaction mixture via a gas which comprises hydrogen, thereby preparing 2,7-octadienyl derivatives.

2. The telomerization process as claimed in claim 1, wherein said feedstock is a mixture of hydrocarbons which comprises the noncyclic olefins having at least two conjugated double bonds in a mixture with other hydrocarbons.

3. The telomerization process as claimed in claim 2, wherein the mixture of hydrocarbons contains up to 5% by mass of alkynes.

4. The telomerization process as claimed in claim 3, wherein the mixture of hydrocarbons comprises alkynes selected from the group consisting of vinylacetylene and 1-butyne.

5. The telomerization process as claimed in claim 3, wherein a portion of the alkynes present in the mixture is hydrogenated selectively before telomerization.

6. The telomerization process as claimed in claim 3, wherein the hydrogen source adds sufficient hydrogen to the overall process that the molar ratio of hydrogen to alkyne is at least 1 to 1.

7. The telomerization process as claimed in claim 2, wherein the mixture of hydrocarbons contains over 90% by mass of $C_4$ hydrocarbons.

8. The telomerization process as claimed in claim 1, wherein the noncyclic olefins having at least two conjugated double bonds are 1,3-butadiene or isoprene.

9. The telomerization process as claimed in claim 1, wherein the catalyst is a palladium-carbene complex which contains a carbene ligand of formula VIII:

VIII where $R^2$; $R^3$: are the same or different and are each independently
a) linear, branched, substituted or unsubstituted, cyclic or alicyclic alkyl groups having from 1 to 24 carbon atoms, or
b) substituted or unsubstituted, mono- or polycyclic aryl groups having from 6 to 24 carbon atoms or
c) mono- or polycyclic, substituted or unsubstituted heterocycle having from 4 to 24 carbon atoms and at least one heteroatom selected from the group consisting of N, O and S, and R', R": are the same or different and are each independently
hydrogen, alkyl, aryl heteroaryl, —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferocenyl, —SO$_3$H, —PO$_3$H$_2$, where alkyl groups contain 1-24 carbon atoms and the aryl and heteroaryl groups from 5 to 24 carbon atoms, and the R' and R" radicals ay also be part of a bridging aliphatic or aromatic ring.

10. The telomerization process as claimed in claim 1, wherein the telomerization catalyst is a palladium-carbene complex which contains a carbene ligand of formula IX, X, XI or XII:

IX

X

XI

XII where $R^2$; $R^3$: are the same or different and are each independently
a) linear, branched substituted or unsubstituted, cyclic or alicyclic alkyl groups having from 1 to 24 carbon atoms, or
b) substituted or unsubstituted, mono- or polycyclic aryl groups having from 6 to 24 carbon atoms or
c) mono- or polycyclic, substituted or unsubstituted heterocycle having from 4 to 24 carbon atoms and at least one heteroatom selected from the group consisting of N, O and S, and

$R^4$, $R^5$, $R^6$, $R^7$: are the same or different and are each independently
hydrogen, alkyl, aryl, heteroaryl, —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH$_2$, —NH(alkyl)-, —N(alkyl)$_2$-, —NH(aryl)-, —N(alkyl)$_2$-, —F, —Cl, —Br, —I, —OH, —CF$_3$, —NO$_2$, -ferrocenyl, —SO$_3$H, —PO$_3$H$_2$, where the alkyl groups contain 1-24 carbon atoms and the aryl and heteroaryl groups from 5 to 24 carbon atoms, and the $R^4$, $R^5$, $R^6$ and $R^7$ radicals may also be part of a bridging aliphatic or aromatic ring.

11. The telomerization process as claimed in claim 9, wherein the ratio of ligand to palladium [mol/mol] in the reaction mixture is from 0.01:1 to 250:1.

12. The telomerization process as claimed in claim 1, wherein the at least one nucleophile VII is at least one compound selected from the group consisting of those which have formulae VIIa, VIIb and VIIc VIIa VIIb VIIc in which $R^{1a}$ and $R^{1b}$ are each independently selected from the group consisting of hydrogen, a linear, branched or cyclic $C_1$ to $C_{22}$-alkyl group, -alkenyl group or -alkynyl group, a $C_5$ to $C_{18}$-aryl group or a —CO-alkyl-($C_1$-$C_8$) group or a —CO-aryl-($C_5$-$C_{10}$) group, where these groups may contain substituents selected from the group consisting of —CN, —COOH, —COO-alkyl-($C_1$-$C_8$), —CO-alkyl-($C_1$-$C_8$), -aryl-($C_5$-$C_{10}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$ and —NO$_2$, and where $R^{1a}$ and $R^{1b}$ radicals may be joined together via covalent bonds.

13. The telomerization process as claimed in claim 12, wherein the at least one nucleophile (VII) is at least one compound selected from the group consisting of water, alcohols, phenols, polyols, carboxylic acids, ammonia, primary and secondary amines.

14. The telomerization process as claimed in claim 1, wherein the telomerization is conducted in the presence of a solvent.

15. The telomerization process as claimed in claim 1, wherein the telomerization is conducted in the presence of a solvent and the solvent is the at least one nucleophile (VII) and/or an inert organic solvent.

16. The telomerization process as claimed in claim 1, wherein the hydrogen source is added during the telomerization reaction.

17. The telomerization process as claimed in claim 1, wherein the telomerization process further comprises a catalyst recycling step and the hydrogen source is added to the telomerization process in the catalyst step.

* * * * *